(12) United States Patent
Benedict et al.

(10) Patent No.: US 10,245,147 B2
(45) Date of Patent: Apr. 2, 2019

(54) BONE VOID PLUGS AND METHODS OF USE

(71) Applicant: ARTHREX, INC., Naples, FL (US)

(72) Inventors: Robert Benedict, Fort Myers, FL (US); Brandon Roller, Naples, FL (US)

(73) Assignee: ARTHREX, INC., Naples, FL (US)

( * ) Notice: Subject to any disclaimer, the term of this patent is extended or adjusted under 35 U.S.C. 154(b) by 85 days.

(21) Appl. No.: 15/377,003

(22) Filed: Dec. 13, 2016

(65) Prior Publication Data

US 2017/0086979 A1 Mar. 30, 2017

Related U.S. Application Data

(62) Division of application No. 14/314,513, filed on Jun. 25, 2014.

(60) Provisional application No. 61/844,114, filed on Jul. 9, 2013.

(51) Int. Cl.
| | |
|---|---|
| *A61F 2/30* | (2006.01) |
| *A61F 2/28* | (2006.01) |
| *A61F 2/08* | (2006.01) |
| *A61B 17/88* | (2006.01) |
| *A61F 2/46* | (2006.01) |

(52) U.S. Cl.
CPC ...... *A61F 2/30723* (2013.01); *A61B 17/8808* (2013.01); *A61F 2/0811* (2013.01); *A61F 2/28* (2013.01); *A61F 2/30767* (2013.01); *A61F 2002/0864* (2013.01); *A61F 2002/0888* (2013.01); *A61F 2002/2839* (2013.01); *A61F 2002/30062* (2013.01); *A61F 2002/30225* (2013.01); *A61F 2002/30235* (2013.01); *A61F 2002/30772* (2013.01); *A61F 2002/30881* (2013.01); *A61F 2002/4631* (2013.01); *A61F 2210/0085* (2013.01)

(58) Field of Classification Search
CPC .......... A61F 2/30; A61F 2/30723; A61F 2/28; A61F 2/0811
See application file for complete search history.

(56) References Cited

U.S. PATENT DOCUMENTS

| | | | |
|---|---|---|---|
| 1,989,714 A | | 2/1935 | Statham |
| 4,697,584 A | | 10/1987 | Haynes |
| 7,585,357 B2 | | 9/2009 | Tanner et al. |
| 8,177,738 B2 | | 5/2012 | Schmieding et al. |
| 8,377,089 B2 | | 2/2013 | Lipchitz et al. |
| 2002/0151979 A1 | | 10/2002 | Lambrecht et al. |
| 2004/0127905 A1 | | 7/2004 | Lim et al. |
| 2010/0125240 A1 | * | 5/2010 | Spedden ............ A61B 17/0057 604/37 |
| 2011/0144757 A1 | * | 6/2011 | Linares ................ A61F 2/32 623/18.11 |
| 2013/0189313 A1 | * | 7/2013 | Stewart ............... A61L 24/0015 424/400 |

(Continued)

FOREIGN PATENT DOCUMENTS

EP 2269526 A1 1/2011

*Primary Examiner* — Jason-Dennis N Stewart
(74) *Attorney, Agent, or Firm* — Carlson, Gaskey & Olds

(57) ABSTRACT

A bone void plug includes a plug body that extends along a longitudinal axis between a proximal face and a distal opening and a recessed opening that extends from the distal opening toward the proximal face. The recessed opening is configured to receive a bone void filler.

20 Claims, 5 Drawing Sheets

(56) References Cited

U.S. PATENT DOCUMENTS

2014/0195005 A1\* 7/2014 McKay ................... A61F 2/28
                                              623/23.63

\* cited by examiner

BONE VOID PLUGS AND METHODS OF USE

CROSS-REFERENCE TO RELATED APPLICATIONS

This is a divisional of U.S. patent application Ser. No. 14/314,513, which was filed on Jun. 25, 2014, which claims priority to U.S. Provisional Application No. 61/844,114, which was filed on Jul. 9, 2013, the disclosures of which are incorporated by reference in their entirety herein.

BACKGROUND

This disclosure relates to a surgical device, and more particularly to a bone void plug that may be utilized to temporarily or permanently plug or dam a bone void.

Reconstructive procedures are commonly performed to diagnose and treat musculoskeletal injuries. For example, ligament reconstruction, bone resurfacing and/or joint replacement may be performed utilizing a variety of arthroscopic reconstruction procedures. Many reconstructive procedures, such as anterior cruciate ligament (ACL) reconstruction, often require drilling bone sockets, tunnels or other openings in bone for accommodating one or more surgical fixation devices. The formation of these openings creates a bone void.

It may become necessary to fill bone voids with a bone void filler, such as during a revision procedure, in order to stabilize the bone or restore the bone as close as possible to its original anatomical structure. Advancements in this field of technology are desirable.

SUMMARY

A bone void plug according to an exemplary aspect of the present disclosure includes, among other things, a plug body that extends along a longitudinal axis between a proximal face and a distal opening and a recessed opening that extends from the distal opening toward the proximal face, the recessed opening configured to receive a bone void filler.

In a further non-limiting embodiment of the foregoing bone void plug, the plug body is circumferentially disposed about the longitudinal axis.

In a further non-limiting embodiment of either of the foregoing bone void plugs, the recessed opening extends from the distal opening to an inner surface of the proximal face.

In a further non-limiting embodiment of any of the foregoing bone void plugs, at least one port is formed through the proximal face.

In a further non-limiting embodiment of any of the foregoing bone void plugs, the port includes a passageway and a septum.

In a further non-limiting embodiment of any of the foregoing bone void plugs, the septum is received in a recess formed inside the proximal face, and the recess connects the passageway to the recessed opening.

In a further non-limiting embodiment of any of the foregoing bone void plugs, the septum includes an expandable passageway that is aligned with the passageway.

In a further non-limiting embodiment of any of the foregoing bone void plugs, a plurality of protrusions extend radially outwardly from the plug body.

In a further non-limiting embodiment of any of the foregoing bone void plugs, the proximal face includes a central opening, and a flexible member is accommodated within the central opening.

In a further non-limiting embodiment of any of the foregoing bone void plugs, the flexible member is a graft that is fixated to the plug body.

A method according to another exemplary aspect of the present disclosure includes, among other things, positioning a bone void plug relative to a bone void, inserting a bone void filler into the bone void and blocking displacement of the bone void filler out of the bone void with the bone void plug.

In a further non-limiting embodiment of the foregoing method, the method includes fixating a flexible member to the bone void plug prior to the positioning step. The inserting step includes injecting the bone void filler around the flexible member within the bone void.

In a further non-limiting embodiment of either of the foregoing methods, the method includes inserting a guide pin into a bone, positioning a cannulated drill bit over the guide pin and reaming the bone void with the cannulated drill bit.

In a further non-limiting embodiment of any of the foregoing methods, the positioning step includes pushing or tapping the bone void plug into an opening of the bone void.

In a further non-limiting embodiment of any of the foregoing methods, the opening is located at a junction between an exterior surface of a bone and the bone void, and the positioning step includes positioning the bone void plug such that a proximal face of the bone void plug is flush with the exterior surface.

In a further non-limiting embodiment of any of the foregoing methods, the inserting step includes inserting a delivery tool through a port of the bone void plug.

In a further non-limiting embodiment of any of the foregoing methods, the method includes visualizing the bone void filler through a second port of the bone void plug.

In a further non-limiting embodiment of any of the foregoing methods, the positioning step includes positioning a malleable distal face of the bone void plug against an exterior surface of the bone such that the malleable distal face conforms to a shape of the exterior surface and covers an opening of the bone void.

In a further non-limiting embodiment of any of the foregoing methods, the bone void extends inside of a bone between an opening and a floor. The positioning step includes inserting the bone void plug into the opening such that a proximal face of the bone void plug sits flush with an exterior surface of the bone and a plug body of the bone void plug extends in a direction toward the floor and contacts a peripheral wall of the bone void.

A bone void plug according to another exemplary aspect of the present disclosure includes, among other things, a plug body disposed about a central axis between a proximal face and a distal face. The distal face includes a malleable material. A port extends from the proximal face to the distal face. A septum is disposed inside the port.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

Among other features, this disclosure relates to a bone void plug that can be used to plug a bone void or some other tissue void. The exemplary bone void plugs of this disclosure may be utilized to temporarily or permanently plug a bone void. The bone void plug acts as a dam to inhibit displacement of bone void filler that has been inserted into the bone void. These and other features are described in greater detail below.

FIGS. 1A, 1B, 1C and 1D illustrate a bone void plug 10. The bone void plug 10 is configured to plug a bone void by blocking the escape of bone void filler out of the bone void and into a surrounding joint space before the bone void filler has time to harden or cure. The exemplary bone void plug 10 may include a plug body 12 that extends along a longitudinal axis A (see FIGS. 1B and 1D) between a proximal face 14 and a distal opening 16. In one embodiment, the plug body 12 is circumferentially disposed about the longitudinal axis A. However, the bone void plug 10 could embody other shapes and configurations. In addition, it should be appreciated that the size of the bone void plug 10 can vary to accommodate bone voids of any size.

In one embodiment, the proximal face 14 extends perpendicular to the plug body 12 of the bone void plug 10 and is generally flat. Once installed, the proximal face 14 may sit flush with an outer surface of a bone. The plug body 12 may extend into the bone void that is to be backfilled with a bone void filler. In other words, the plug body 12 is insertable inside of bone.

Figure 1A:
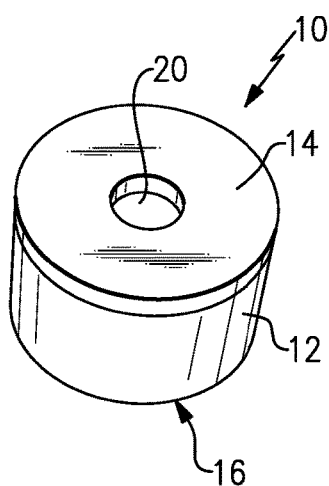
FIG. 1A illustrates a bone void plug according to a first embodiment of this disclosure.
Figure 1B:
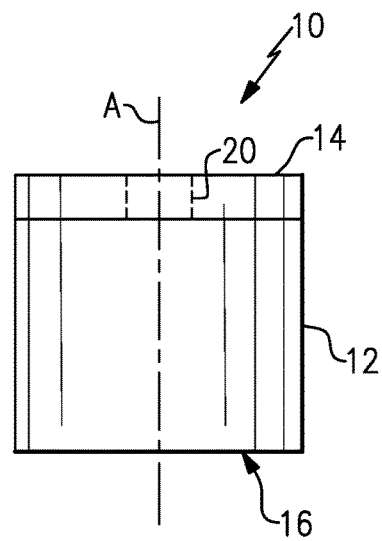
FIG. 1B illustrates a front view of the bone void plug of FIG. 1A.
Figure 1C:
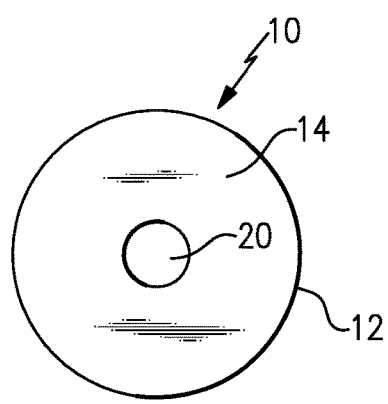
FIG. 1C illustrates a top view of the bone void plug of FIG. 1A.
Figure 1D:
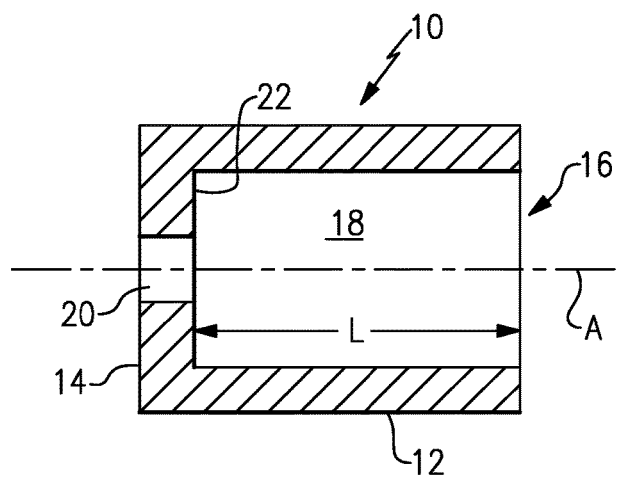
FIG. 1D illustrates a cross-sectional view of the bone void plug of FIG. 1A.

As best shown in FIG. 1D, a recessed opening 18 may extend from the distal opening 16 toward the proximal face 14. In one embodiment, the recessed opening includes a length L that extends an entire distance between the distal opening 16 and an inner surface 22 of the proximal face 14 (see FIG. 1D). In other words, in one non-limiting embodiment, the bone void plug 10 is a close-ended sleeve with the proximal face 14 representing the closed end of the sleeve and the distal opening 16 representing the open end of the sleeve that opens into the recessed opening 18. In another embodiment, the bone void plug 10 is shaped similar to a cap.

A port 20 may be formed through the proximal face 14. The port 20 provides access to the recessed opening 18. In one embodiment, the port 20 may be sized and shaped to accommodate a delivery tool for delivering a bone void filler, the details of which are further discussed below.

The bone void plug 10 may be manufactured from a variety of materials. In one embodiment, the bone void plug 10 is made of a resorbable material. Non-limiting examples of suitable resorbable materials include PLDLA (poly-1 d-lactide), PLLA (poly-1-lactide), bio-composite materials (PLDLA/Beta tricalcium phosphate), or ceramics. In another embodiment, the bone void plug 10 is made of non-resorbable materials. Non-limiting examples of non-resorbable materials include PEEK (Polyether ether ketone), metal, or other materials. In yet another embodiment, the bone void plug 10 is made of PBO (poly-p-phenylene-2,6-benzobisoxazole). The bone void plug 10 may also be constructed of hard (molded/machined PLLA, ABS, etc.) or malleable (low molecular weight PVA, silicone, etc.) materials.

Figure 2:
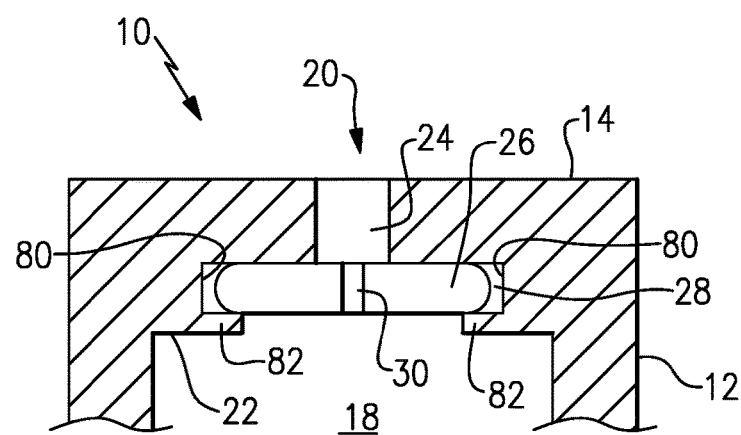
FIG. 2 illustrates a port of a bone void plug.

FIG. 2 illustrates one non-limiting embodiment of a port 20 of a bone void plug 10. In this embodiment, the port 20 includes a passageway 24 and a septum 26. The septum 26 is designed to provide an air-tight seal that prevents egress of material inside the recessed opening 18 through the port 20 during insertion and removal of a delivery tool into and out of the recessed opening 18.

The septum 26 may be received within a recess 28 formed inside the proximal face 14 of the bone void plug 10. In one embodiment, the recess 28 includes opposing walls 80 and legs 82 that protrude from the walls 80. The legs 82 hold the septum 26 within the recess 28. In another embodiment, the legs 82 form a portion of the inner surface 22 of the proximal face 14.

The recess 28 may connect the passageway 24 to the recessed opening 18. In one embodiment, the septum 26 is formed of an elastomeric material, such as silicone rubber. The septum 26 includes a passageway 30 that is aligned with the passageway 24. The passageway 30 may expand in response to insertion of a delivery tool and contract in response to removal of the delivery tool.

Figure 3A:
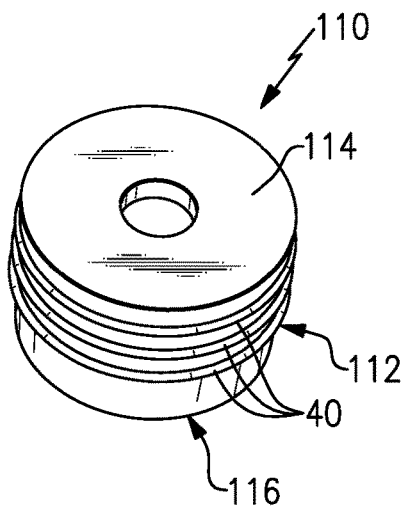
FIGS. 3A and 3B illustrate a bone void plug according to a second embodiment of this disclosure.
Figure 3B:
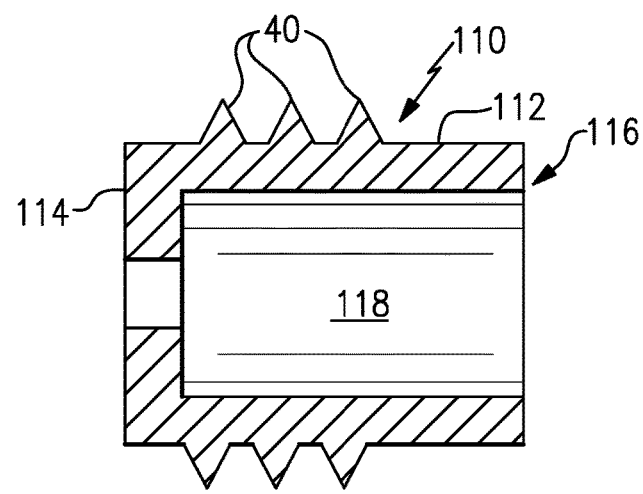

FIGS. 3A and 3B illustrate another embodiment of a bone void plug 110. In this disclosure, like reference numerals designate like elements where appropriate and reference numerals with the addition of 100 or multiples thereof designate modified elements that are understood to incorporate the same features and benefits of the corresponding original elements.

In this embodiment, the bone void plug 110 includes a plug body 112 that extends between a proximal face 114 and a distal opening 116. A recessed opening 118 extends from the distal opening 116 toward the proximal face 114 (see FIG. 3B).

The plug body 112 may include one or more protrusions 40 that can improve fixation of the bone void plug 110 relative to a bone void. The protrusions 40 extend radially outwardly from the plug body 112. The protrusions 40 may include circumferential ledges, ridges, legs, barbs, prongs or any feature designed to aid the fixation strength of the bone void plug 10.

Figure 4:
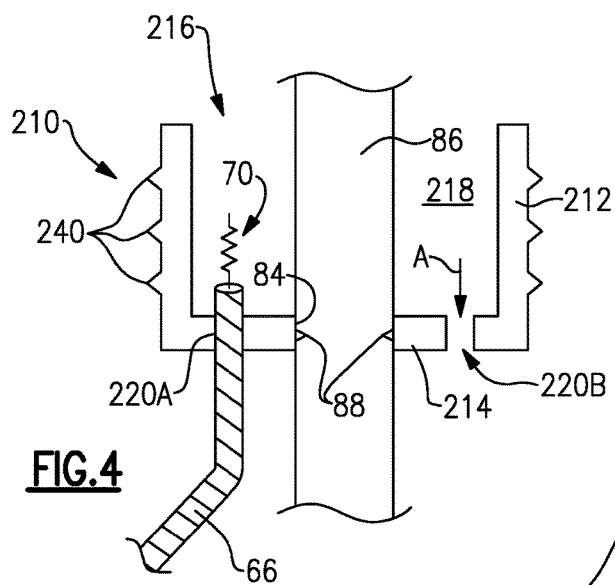
FIG. 4 illustrates a bone void plug according to yet another embodiment of this disclosure.

FIG. 4 illustrates yet another bone void plug 210. The bone void plug 210 includes a plug body 212 that extends between a proximal face 214 and a distal opening 216. A recessed opening 218 extends from the distal opening 216 toward the proximal face 214. The plug body 212 may include one or more protrusions 240 that can improve fixation of the bone void plug 210 relative to bone. The protrusions 240 extend radially outwardly from the plug body 212, in one embodiment.

The bone void plug 210 may additionally include a central opening 84 formed through the proximal face 214. In one embodiment, a flexible member 86 is fixated with the bone void plug 210. The flexible member 86 may be accommodated within the central opening 84. In one embodiment, the flexible member 86 is a graft, such as an autograft, allograft or synthetic graft. In another embodiment, the flexible member 70 includes a suture, such as a suture strand or suture tape. Other flexible members may be fixated to the bone void plug 210 within the scope of this disclosure.

In one non-limiting embodiment, the central opening 84 includes fixation features 88, such as teeth or barbs, which protrude inwardly from the central opening 84. The fixation features 88 may grip the flexible member 86 to temporarily fixate it relative to the bone void plug 210.

In another embodiment, the proximal face 214 of the bone void plug 210 includes multiple ports 220A, 220B. Although two ports are shown in FIG. 4, the bone void plug 210 could employ any number of ports. The ports 220A, 220B are formed through the proximal face 214 and provide access to the recessed opening 218.

In one embodiment, the first port 220A accommodates a delivery tool 66 for delivering a bone void filler 70. The bone void filler 70 can be injected into a bone void around the flexible member 86 using the first port 220A. Once the bone void filler 70 cures, the flexible member 86 may be substantially fixated to the bone void plug 210.

In another embodiment, the second port 220B is an air vent that allows air A to escape through the bone void plug 210. The second port 220B may also provide visual confirmation that a bone void has been filled with the bone void filler 70. For example, a surgeon would be alerted to stop injecting the bone void filler 70 once the bone void filler 70 can be seen through the second port 220B.

It should be understood that the ports 220A, 220B could serve any of the functions described above. For example, in one non-limiting embodiment, one of the ports 220A, 220B accommodates the delivery tool 66 while the other port 220A, 220B acts as the air vent/visualization port.

FIGS. 5-9 schematically illustrate an exemplary method for filling a bone void. The exemplary method may utilize a bone void plug such as any of those described above and illustrated in FIGS. 1A, 1B, 1C, 1D, 2, 3A, 3B, and 4. For example, any of the exemplary bone void plugs 10, 110, 210 may be used to inhibit displacement of a bone void filler out of a bone void formed in the bone.

In one non-limiting embodiment, the method illustrated by FIGS. 5-9 is performed as part of a revision surgery to reconstruct an ACL footprint in response to a failed original repair. In another embodiment, the method repairs damaged bone. The method could also have many other applications. Furthermore, although specific steps are illustrated in FIGS. 5-9, the method could include greater or fewer steps which may be performed in any order within the scope of this disclosure.

Figure 5:
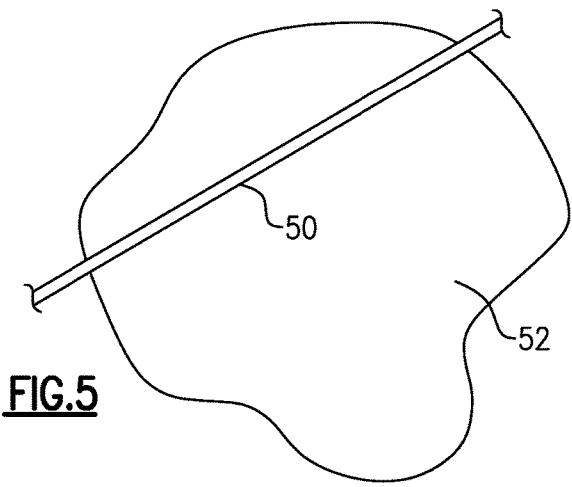
FIGS. 5, 6, 7, 8 and 9 schematically illustrate a method for filling a bone void.

As illustrated in FIG. 5, the method may begin by inserting a guide pin 50 into a bone 52. The bone 52 could be a femur or any other bone or tissue. A surgeon will be able to select an appropriate positioning and/or placement of the guide pin 50 and could use fluoroscopic guidance and/or a targeting guide to achieve proper placement.

Figure 6:
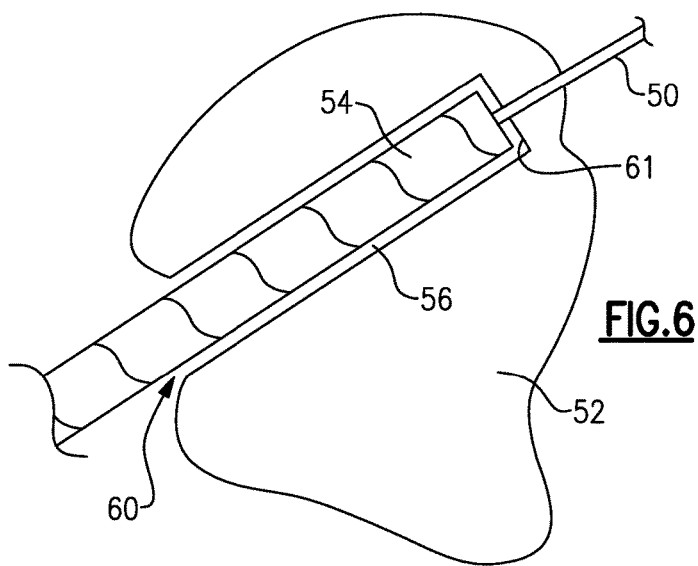

Once the guide pin 50 has been positioned, a cannulated drill bit 54 may be placed over the guide pin 50 to ream a bone void 56 into the bone 52. This is shown in FIG. 6. The size of the guide pin 50 and the cannulated drill bit 54 may vary depending upon the size of the patient and the amount of bone that needs removed, among other criteria. Once the bone void 56 is created, the cannulated drill bit 54 and guide pin 50 may be removed from the bone 52.

Alternatively, the bone void 56 may be formed without using a guide pin by simply reaming the bone 52 with a drill bit or other tool. In yet another embodiment, the bone void 56 is a preexisting defect in the bone 52 such that drilling and reaming operations are not necessary to form the bone void 56. The bone void 56 may extend between an opening 60 and a floor 61, in one embodiment.

Figure 7:
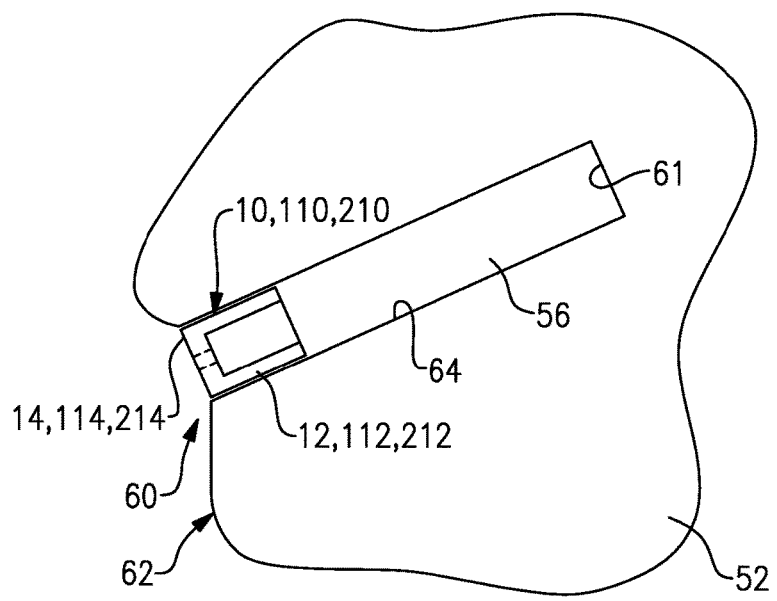

Next, as illustrated by FIG. 7, a bone void plug 10, 110, 210 may be inserted into the bone void 56. In one embodiment, the bone void plug 10, 110, 210 is a push-in device that may be pushed into the bone void 56 by hand or with a tool. Alternatively, the bone void plug 10, 110, 210 could be tapped in or screwed into the bone void 56.

In one embodiment, the bone void plug 10, 110, 210 is positioned near the opening 60 of the bone void 56. The opening 60 may be located at a junction between an exterior surface 62 of the bone 52 and the bone void 56. The proximal face 14, 114, 214 of the bone void plug 10, 110, 210 may sit flush relative to the exterior surface 62. The plug body 12, 112, 212 may extend into the bone void 56 in a direction toward the floor 61 and contact a peripheral wall 64 of the bone void 56.

In one embodiment, if the bone void plug 210 of FIG. 4 is used, a flexible member 86 may be fixated to the bone void plug 210 prior to positioning the bone void plug 210 into the opening 60 (see FIG. 4). The fixation features 88 grip the flexible member 86 to temporarily fixate it relative to the bone void plug 210.

Figure 8:
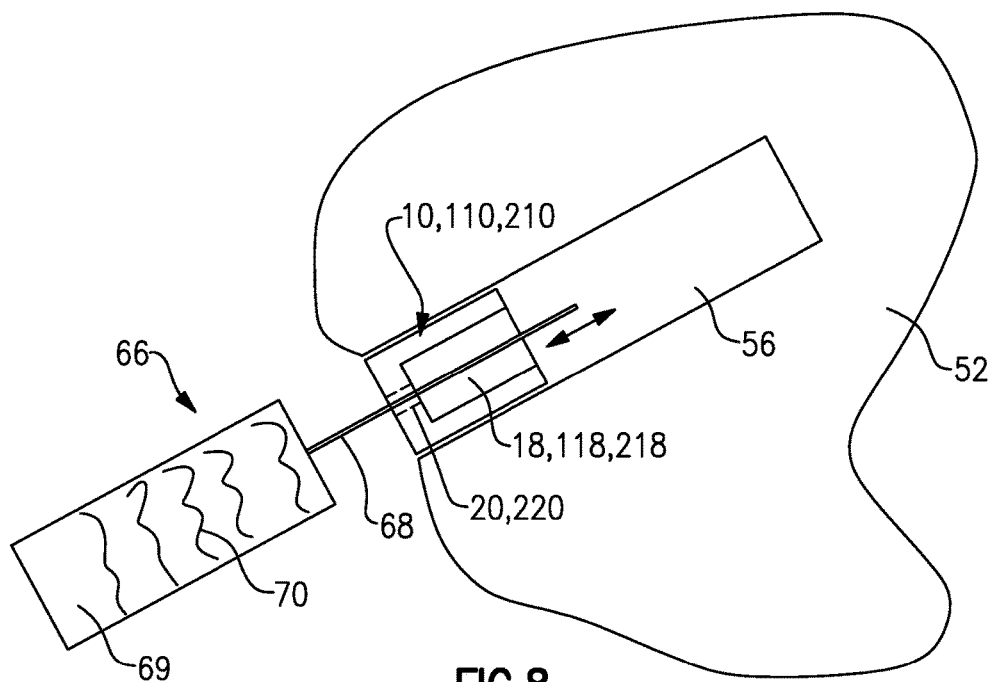

Referring to FIG. 8, a delivery tool 66 may be inserted through the port 20, 220 of the bone void plug 10, 110, 210 and into the recessed opening 18, 118, 218. The delivery tool 66 may include a chamber 69 that carries a bone void filler 70 for filling the bone void 56. In one embodiment, the delivery tool 66 includes a needle 68 that is insertable through the port 20, 220, and optionally through a septum (see feature 26 of FIG. 2), for delivering the bone void filler 70 into the recessed opening 18, 118, 218 and then into the bone void 56. The port 20, 220 may prevent leakage of materials or substances back through the bone void plug 10, 110, 210 during insertion and removal of the delivery tool 66.

In one embodiment, again assuming the bone void plug 210 of FIG. 4 is employed, the bone void filler 70 is injected into the bone void 56 and may flow around the flexible member 86 (see FIG. 4). Once the bone void filler 70 cures, the flexible member 86 is substantially fixated to the bone void plug 210.

Figure 9:
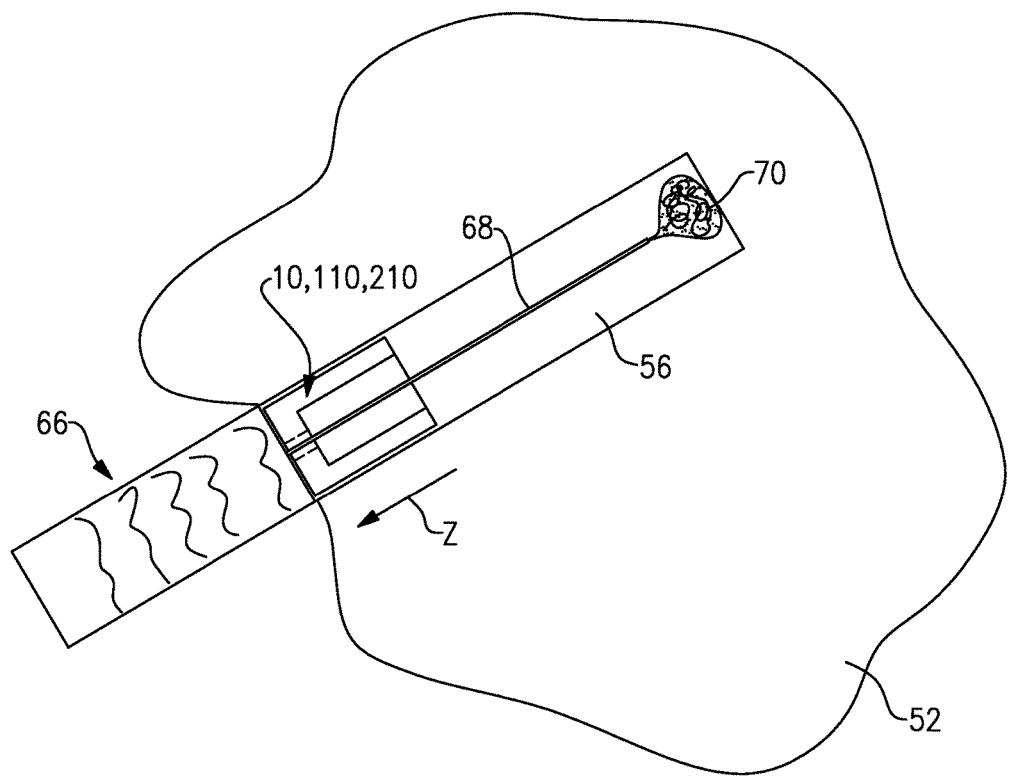

Finally, as shown in FIG. 9, all or portions of the bone void 56 may be backfilled with the bone void filler 70. The bone void filler 70 may include a variety of substances for plugging the bone void 56. Non-limiting examples of suitable bone void fillers include calcium phosphate bone cements, biologics, or any other filler materials. The bone void filler 70 may also be either injectable or non-injectable bone filler materials.

The bone void plug 10, 110, 210 "dams" the bone void 56 and allows the bone void filler 70 to cure, set, harden, etc. inside the bone void 56 without risk of displacement from within the bone void 56. In other words, the bone void plug 10, 110, 210 inhibits displacement of the bone void filler 70 out of the bone void 56 in a direction Z prior to its hardening, setting, curing, etc.

The bone void plug 10, 110, 210 may optionally be removed once the bone void filler 70 has cured. Additional revision repairs may then be performed. Once removed, the bone void plug 10, 110, 210 could leave a slight imprint in the bone void filler 70, but generally leaves a relatively flat surface for eventual or immediate surgical need.

Figure 10:
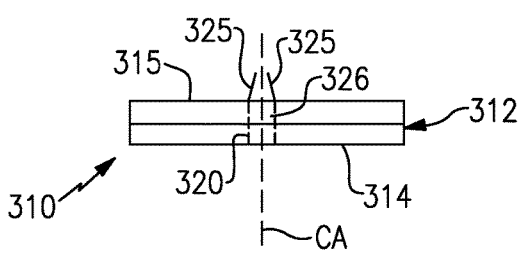
FIG. 10 illustrates a bone void plug according to yet another embodiment of this disclosure.

FIG. 10 illustrates yet another bone void plug 310 configured to plug a bone void by blocking displacement of bone void filler out of the bone void. The exemplary bone void plug 310 may include a plug body 312 disposed about a central axis CA between a proximal face 314 and a distal face 315. In one embodiment, the plug body 312 is circumferentially disposed about the central axis CA. In another embodiment, the plug body 312 is a flat disk.

In one embodiment, the proximal face 314 and the distal face 315 are made of different materials. For example, the proximal face 314 may be made of a rigid material and the distal face 315 may be made of a malleable material. The malleable nature of the distal face 315 allows it to conform to a shape of the surface it is pressed against.

A port 320 extends through the plug body 312 from the proximal face 314 to the distal face 315. The port 320 may be sized and shaped to accommodate a delivery tool for delivering a bone void filler into a bone void. A septum 326 may be disposed inside the port 320. The septum 326 provides an air-tight seal that prevents egress of material through the port 320 during insertion and removal of a delivery tool.

In one embodiment, the septum 326 includes a plurality of flaps 325. In one non-limiting embodiment, the flaps 325 spread apart to open the port 320 when a tool is inserted through the septum 326 and collapse on top of one another when the tool is removed to close the port 320.

Figure 11:
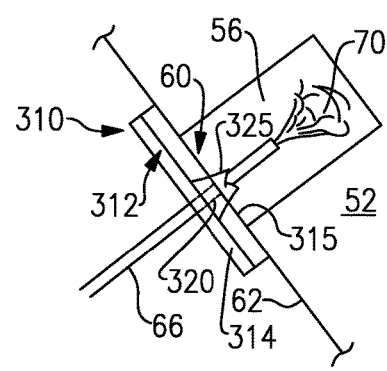
FIG. 11 schematically illustrates a method of using the bone void plug of FIG. 10.

Referring to FIG. 11, the bone void plug 310 may be positioned relative to bone void 56 of a bone 52 such that the distal face 315 presses against an exterior surface 62 of the bone 52. The malleable distal face 315 may conform to the shape of the exterior surface 62 to seal an opening 60 of the bone void 56. In one embodiment, the plug body 312 of the bone void plug 310 is wider than the opening 60 of the bone void 56 such that the bone void plug 310 rests substantially outside of the bone void 56. Once positioned, a delivery tool 66 may be inserted through the port 320 to deliver a bone void filler 70.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A method, comprising:
    positioning a bone void plug relative to a bone void;
    inserting a bone void filler into the bone void,
    wherein at least a portion of the bone void filler backfills a recessed opening of the bone void plug during the inserting; and
    blocking displacement of the bone void filler out of the bone void with a proximal face of the bone void plug.

2. The method as recited in claim 1, comprising fixating a flexible member to the bone void plug prior to positioning the bone void plug, and wherein inserting the bone void filler includes injecting the bone void filler around the flexible member and into the bone void.

3. The method as recited in claim 1, comprising:
    inserting a guide pin into a bone;
    positioning a cannulated drill bit over the guide pin; and
    reaming the bone void with the cannulated drill bit.

4. The method as recited in claim 1, wherein positioning the bone void plug includes pushing the bone void plug into an opening of the bone void.

5. The method as recited in claim 4, wherein the opening is located at a junction between an exterior surface of a bone and the bone void, and positioning the bone void plug includes positioning a proximal face of the bone void plug so it is flush with the exterior surface.

6. The method as recited in claim 1, wherein positioning the bone void plug includes screwing the bone void plug into an opening of the bone void.

7. The method as recited in claim 1, wherein inserting the bone void filler includes inserting a delivery tool through a port of the bone void plug.

8. The method as recited in claim 1, wherein the bone void extends inside of a bone between an opening and a floor, and positioning the bone void plug includes:
    inserting the bone void plug into the opening such that a proximal face of the bone void plug sits flush with an exterior surface of the bone and a plug body of the bone void plug extends in a direction toward the floor and contacts a peripheral wall of the bone void.

9. A method, comprising:
    inserting a bone void plug into a bone void of a bone;
    after inserting the bone void plug into the bone void, inserting a delivery tool through a port of the bone void plug;
    backfilling the bone void with a bone void filler carried by the delivery tool; and
    wherein the bone void plug dams the bone void and allows the bone void filler to cure inside the bone without displacing from the bone void.

10. The method as recited in claim 9, comprising removing the bone void plug from the bone void after the bone void filler has cured.

11. The method as recited in claim 9, wherein inserting the bone void plug includes positioning the bone void plug such that a proximal face of the bone void plug sits flush relative to an exterior surface of the bone, a plug body of the bone void plug extends toward a floor of the bone void, and the plug body contacts a peripheral wall of the bone void.

12. The method as recited in claim 9, wherein the bone void filler includes a calcium phosphate bone cement.

13. The method as recited in claim 9, wherein the bone void filler includes a biologic.

14. The method as recited in claim 9, wherein inserting the delivery tool includes:
    inserting a needle of the delivery tool through the port and through a recessed opening of the bone void plug; and
    injecting the bone void filler through the needle and into the bone void.

15. The method as recited in claim 14, wherein inserting the delivery tool includes inserting the needle through a septum of the bone void plug.

16. The method as recited in claim 9, wherein the bone void plug includes:

a plug body that extends along a longitudinal axis between a proximal face and a distal opening;

a recessed opening that extends from said distal opening toward the proximal face, the recessed opening configured to receive the bone void filler; and a port formed through the proximal face and including a passageway and a septum.

17. The method as recited in claim 9, wherein the bone void plug includes:

a plug body extending between a proximal face and a distal opening;

a recessed opening extending from the distal opening to an inner surface of the proximal face;

a septum received within the port; and a plurality of protrusions that extend outwardly from the plug body and are configured to engage a bone wall surrounding the bone void.

18. The method as recited in claim 17, wherein the septum includes a passageway that expands in response to inserting the delivery tool through the septum and contracts in response to removing the delivery tool from the septum.

19. A method, comprising:

inserting a guide pin into a bone;

positioning a cannulated drill bit over the guide pin;

reaming a bone void into the bone with the cannulated drill bit, wherein the bone void includes a floor and an opening at an opposite end of the bone void from the floor;

removing the cannulated drill bit and the guide pin from the bone;

inserting a bone void plug into the opening of the bone void until a proximal face of the bone void plug is substantially flush relative to an exterior surface of the bone, wherein the bone void plug includes a recessed opening that extends from a distal opening of the bone void plug to an inner surface of the proximal face, wherein the bone void plug includes a plurality of protrusions that extend radially outwardly from the bone void plug for augmenting fixation of the bone void plug within the opening;

after inserting the bone void plug into the opening, inserting a needle of a delivery tool through a port and a septum of the bone void plug, wherein the septum includes an expandable passageway that expands as the needle is inserted through the septum; and backfilling the bone void with a bone void filler carried by a chamber of the delivery tool;

wherein the bone void plug dams the opening of the bone void and allows the bone void filler to cure or harden inside the bone without becoming displaced from the bone void, wherein at least a portion of the bone void filler cures or hardens within the recessed opening of the bone void plug.

20. The method as recited in claim 19, comprising performing a revision repair to the bone after the bone void filler cures or hardens.

* * * * *